US00PP24501P2

(12) United States Plant Patent
Sakazaki

(10) Patent No.: US PP24,501 P2
(45) Date of Patent: May 27, 2014

(54) ***PETUNIA* PLANT NAMED 'USTUN48002'**

(50) Latin Name: *Petunia×hybrida*
Varietal Denomination: USTUN48002

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 82 days.

(21) Appl. No.: 13/507,525

(22) Filed: Jul. 5, 2012

(51) Int. Cl.
*A01H 5/00* (2006.01)

(52) U.S. Cl.
USPC ..... Plt./356.13; Plt./356.1; Plt./356.21

(58) Field of Classification Search
USPC ..... Plt./356.1, 356.13, 356.21
See application file for complete search history.

*Primary Examiner* — Susan McCormick Ewoldt
(74) *Attorney, Agent, or Firm* — C. A. Whealy

(57) ABSTRACT

A new and distinct cultivar of *Petunia* plant named 'USTUN48002', characterized by its upright to outwardly spreading and low mounding plant habit; freely branching habit; vigorous growth habit; early and freely flowering habit; large bright red purple-colored flowers with pale green-colored margins; and good garden performance.

1 Drawing Sheet

Botanical designation: *Petunia×hybrida*.
Cultivar denomination: 'USTUN48002'.

BACKGROUND OF THE INVENTION

The present invention relates to a new and distinct cultivar of *Petunia* plant, botanically known as *Petunia×hybrida* and hereinafter referred to by the name 'USTUN48002'.

The new *Petunia* plant is a product of a planned breeding program conducted by the Inventor in Higashiomi, Shiga, Japan and Bonsall, Calif. The objective of the breeding program is to create new freely-branching and mounding *Petunia* plants with early and freely flowering habit, unique attractive flowers and good garden performance.

The new *Petunia* plant originated from a cross-pollination made by the Inventor on May 8, 2009 in Higashiomi, Shiga, Japan of a proprietary seedling selection of *Petunia×hybrida* identified as code number 08P359-01, not patented, as the female, or seed, parent with a proprietary seedling selection of *Petunia×hybrida* identified as code number 09PJ25-5GE, not patented, as the male, or pollen, parent. The new *Petunia* plant was discovered and selected by the Inventor as a single flowering plant within the progeny of the stated cross-pollination in a controlled environment in Bonsall, Calif. on May 27, 2010.

Asexual reproduction of the new *Petunia* plant by vegetative cuttings in a controlled greenhouse environment in Bonsall, Calif. since May 28, 2010 has shown that the unique features of this new *Petunia* plant are stable and reproduced true to type in successive generations.

SUMMARY OF THE INVENTION

Plants of the new *Petunia* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'USTUN48002'. These characteristics in combination distinguish 'USTUN48002' as a new and distinct *Petunia* plant:

1. Upright to outwardly spreading and low mounding plant habit.
2. Freely branching habit.
3. Vigorous growth habit.
4. Early and freely flowering habit.
5. Large bright red purple-colored flowers with pale green-colored margins.
6. Good garden performance.

Plants of the new *Petunia* can be compared to plants of the female parent selection. In side-by-side comparisons conducted in Bonsall, Calif., plants of the new *Petunia* differ primarily from plants of the female parent selection in flower color as plants of the female parent selection have solid red purple-colored flowers.

Plants of the new *Petunia* can be compared to plants of the male parent selection. In side-by-side comparisons conducted in Bonsall, Calif., plants of the new *Petunia* differ from plants of the male parent selection in the following characteristics:

1. Plants of the new *Petunia* are more mounding than plants of the male parent selection.
2. Plants of the new *Petunia* flower earlier than plants of the male parent selection.
3. Plants of the new *Petunia* have larger flowers than plants of the male parent selection.

Plants of the new *Petunia* can be compared to plants of 'BHTUN31501', disclosed in U.S. Plant Pat. No. 21,649. In side-by-side comparisons conducted in Bonsall, Calif., plants of the new *Petunia* differed from plants of 'BHTUN31501' in the following characteristics:

1. Plants of the new *Petunia* were more mounding than plants of 'BHTUN31501'.
2. Plants of the new *Petunia* and 'BHTUN31501' differed in flower color as plants of 'BHTUN31501' had darker-colored flowers.

Plants of the new *Petunia* can also be compared to plants of 'USTUNI153', disclosed in U.S. Plant Pat. No. 14,856. In side-by-side comparisons, plants of the new *Petunia* differed from plants of 'USTUNI153' in the following characteristics:

1. Plants of the new *Petunia* had smaller flowers than plants of 'USTUNI153'.
2. Plants of the new *Petunia* and 'USTUNI153' differed in flower color as plants of 'USTUNI153' had solid pink-colored flowers.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the bottom of the sheet comprises a side perspective view of a typical plant of 'USTUN48002' grown in a container.

The photograph at the top of the sheet is a close-up view of a typical flowering plant of 'USTUN48002'.

DETAILED BOTANICAL DESCRIPTION

The aforementioned photographs and following observations, measurements and values describe plants grown during the spring in 11.4-cm containers in a polyethylene-covered greenhouse and finished in an outdoor nursery in Bonsall, Calif. During the production of the plants, day temperatures averaged 24° C. and night temperatures averaged 18° C. Plants were pinched one time at planting and were six weeks old when the photographs and description were taken. In the following description, color references are made to The Royal Horticultural Society Colour Chart, 2007 Edition, except where general terms of ordinary dictionary significance are used.

Botanical classification: *Petunia×hybrida* 'USTUN48002'.

Parentage:

*Female, or seed, parent.*—Proprietary seedling selection of *Petunia×hybrida* identified as code number 08P359-01, not patented.

*Male, or pollen, parent.*—Proprietary seedling selection of *Petunia×hybrida* identified as code number 09PJ25-5GE, not patented.

Propagation:

*Type.*—Terminal vegetative cuttings.

*Time to initiate roots, summer.*—About three days at temperatures ranging from 17° C. to 29° C.

*Time to initiate roots, winter.*—About four days at temperatures ranging from 17° C. to 21° C.

*Time to produce a rooted plant, summer.*—About 15 days at temperatures ranging from 17° C. to 29° C.

*Time to produce a rooted plant, winter.*—About 20 days at temperatures ranging from 17° C. to 21° C.

*Root description.*—Medium in thickness, fibrous; white in color.

*Rooting habit.*—Freely branching; medium density.

Plant description:

*Plant and growth habit.*—Upright to outwardly spreading and low mounding plant habit; freely branching habit with about 18 primary lateral branches with multiple secondary lateral branches developing per plant; dense and bushy appearance; pinching enhances development of lateral branches; vigorous growth habit.

*Plant height.*—About 14 cm.

*Plant diameter* (*area of spread*).—About 33 cm by 36 cm.

*Lateral branches.*—Length: About 23 cm. Diameter: About 3 mm. Internode length: About 2 cm. Strength: Strong. Texture: Pubescent. Color: Close to 146C.

Foliage description:

*Arrangement.*—Alternate before flowering; opposite after flowers develop; simple.

*Length.*—About 4.5 cm.

*Width.*—About 2.7 cm.

*Shape.*—Elliptical.

*Apex.*—Broadly acute.

*Base.*—Attenuate.

*Margin.*—Entire.

*Texture, upper and lower surfaces.*—Sparsely pubescent.

*Venation pattern.*—Pinnate, arcuate.

*Color.*—Developing leaves, upper surface: Close to 137B. Developing leaves, lower surface: Close to 137C. Fully expanded leaves, upper surface: Close to 137B; venation, close to 146B. Fully expanded leaves, lower surface: Close to 146B; venation, close to 147C.

*Petioles.*—Length: About 8 mm. Diameter: About 3 mm. Texture, upper and lower surfaces: Sparsely pubescent. Color, upper surface: Close to 146C. Color, lower surface: Close to 146D.

Flower description:

*Flower type and habit.*—Single axillary salverform flowers; flowers face mostly upward to outwardly; freely flowering habit with about 18 flower buds and open flowers developing per lateral branch.

*Natural flowering season.*—Long day responsive; long flowering period, plants flower from early spring until frost in the autumn, flowering continuous during this period; early flowering habit, plants begin flowering about six weeks after planting.

*Flower longevity on the plant.*—About three to four days; flowers persistent.

*Fragrance.*—Faint; sweet and floral.

*Flower size.*—Diameter: About 4.3 cm. Depth (height): About 2.7 cm. Throat diameter, distal: About 1 cm by 1.2 cm. Tube length: About 2.5 cm. Tube diameter, proximal: About 3.5 mm.

*Flower buds.*—Length: About 3.2 cm. Diameter: About 1.4 cm. Shape: Oblong. Color: Slightly more lavender grey than N187B.

*Petals.*—Quantity and arrangement: Five petals fused in a single salverform whorl. Petal lobe length (from throat): About 1.7 cm. Petal lobe width: About 1.8 cm. Petal lobe shape: Broadly obovate. Petal lobe apex: Broadly acute; recurved. Petal lobe margin: Entire. Petal lobe texture, upper surface: Smooth, pubescence along margins; velvety. Petal lobe texture, lower surface: Pubescent. Throat texture: Smooth, glabrous. Tube texture: Pubescent. Color: When opening, upper surface: Close to 71B; along the margins, close to 138A. When opening, lower surface: Close to 195B tinged with close to N77D. Fully opened, upper surface: Close to 71B; along the margins, close to 138A; venation, close to 70A; color does not fade with development. Fully opened, lower surface: Close to 196B tinged with close to 75B; venation, close to 146D. Flower throat: Close to 186B to 186C; venation, close to 185C. Flower tube (outside): Close to 186C; venation, close to 146D.

*Sepals.*—Quantity and arrangement: Five sepals fused in a single star-shaped whorl. Length: About 1.7 cm. Width: About 4 mm. Shape: Narrowly spatulate. Apex: Rounded; recurved. Margin: Entire. Texture, upper and lower surfaces: Pubescent. Color, upper surface: Close to 146B. Color, lower surface: Close to 146C.

*Peduncles.*—Length: About 2.5 cm. Width: About 2 mm. Angle: About 60° to 90° from the stem axis. Strength: Strong. Texture: Pubescent. Color: Close to 146D.

*Reproductive organs.*—Stamens: Quantity per flower: Five. Filament length: About 1.6 cm. Filament color: Close to 192D. Anther length: About 2.5 mm. Anther shape: Oval. Anther color: Close to 201D. Pollen amount: Scarce. Pollen color: Close to 201D. Pistils: Quantity per flower: One. Pistil length: About 1.6 cm. Style length: About 1 cm. Style color: Close to 194D. Stigma shape: Rounded. Stigma color: Close to 194C. Ovary color: Close to 145C.

*Seeds and fruits.*—Seed and fruit development has not been observed on plants of the new *Petunia.*

Pathogen & pest resistance: Plants of the new *Petunia* have not been noted to be resistant to pathogens or pests common to *Petunia* plants.

Garden performance: Plants of the new *Petunia* have been observed to have good garden performance and have been observed to tolerate rain, wind and temperatures ranging from about 1° C. to about 40° C.

It is claimed:

1. A new and distinct *Petunia* plant named 'USTUN48002' as illustrated and described.

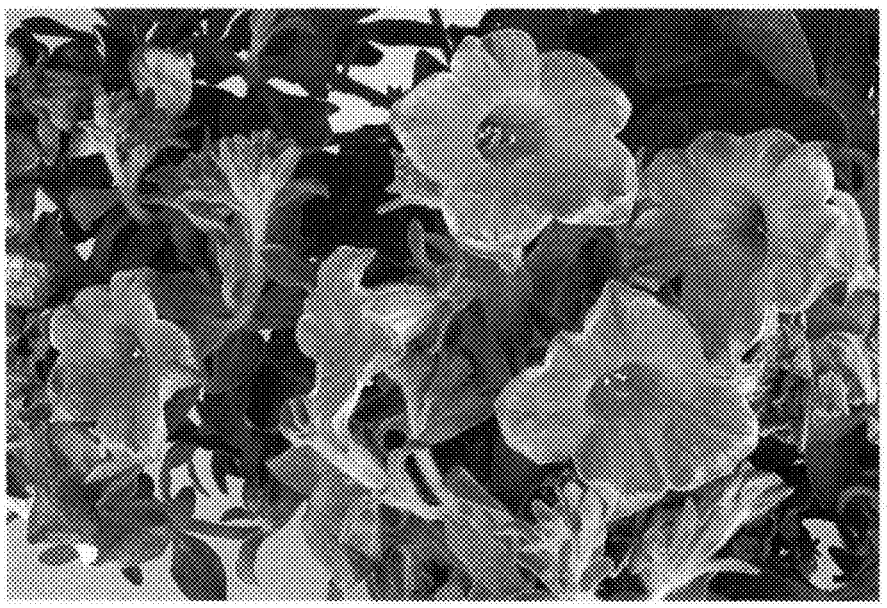
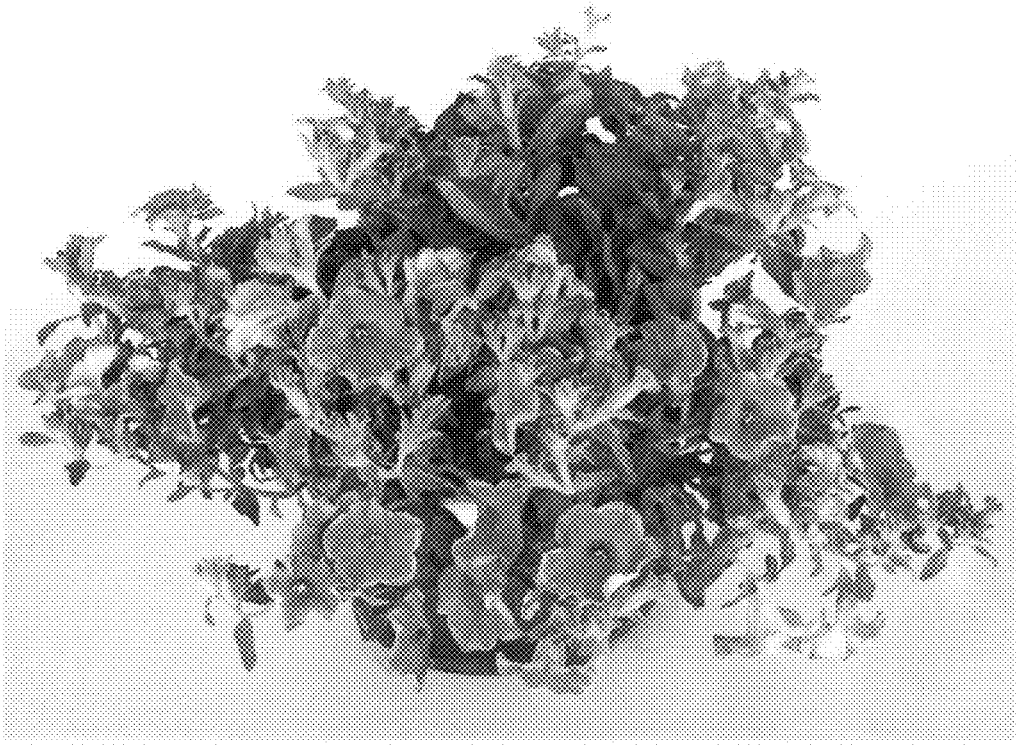

* * * * *